United States Patent [19]

Ng et al.

[11] 4,452,893
[45] Jun. 5, 1984

[54] CELL GROWTH MEDIUM SUPPLEMENT

[75] Inventors: Paul K. Ng, Hercules; Milton B. Dobkin, Lafayette, both of Calif.

[73] Assignee: Cutter Laboratories, Inc., Berkeley, Calif.

[21] Appl. No.: 289,541

[22] Filed: Aug. 3, 1981

[51] Int. Cl.$^3$ .................. C12N 5/00; C12N 5/02; A61K 35/16; A01N 1/00

[52] U.S. Cl. ................ 435/240; 435/244; 435/241; 435/2; 424/101; 260/112 B

[58] Field of Search .............. 435/2, 240, 241, 244, 435/948; 424/101; 260/112 B

[56] References Cited

U.S. PATENT DOCUMENTS

| | | | |
|---|---|---|---|
| 3,128,228 | 4/1964 | Michl | 435/240 |
| 3,953,290 | 4/1976 | Uthne et al. | 435/240 |
| 4,129,648 | 12/1978 | Collier et al. | 424/101 |
| 4,198,479 | 4/1980 | Tytell et al. | 424/85 |
| 4,216,205 | 8/1980 | Radowitz | 424/101 |
| 4,251,510 | 2/1981 | Tankersley | 424/177 |

OTHER PUBLICATIONS

Miles Research Products 1976, Miles Laboratories, Inc., Elkhart, In 46514.
Cohn et al., "Preparation and Properties of Serum and Plasma Proteins," Journal of the American Chemical Society: vol. 68 (1946), pp. 459–475.
Ham et al., "Media and Growth Requirements," Methods in Enzymology, vol. 58 (1979), p. 92.
Maciag et al., "An Endocrine Approach to the Control of Epidermal Growth: Serum–Free Cultivation of Human Keratinocytes," Science vol. 211 (3–1981), pp. 1452–1454.
Rinderknecht et al., "Polypeptides with Nonsuppressible Insulin-like and Cell-Growth Promoting Activities in Human Serum," Proceedings of the National Academy of Sciences, vol. 73(7), (1976), pp. 2365–2369.

Primary Examiner—Thomas G. Wiseman
Assistant Examiner—John Tarcza
Attorney, Agent, or Firm—Theodore J. Leitereg; David J. Aston; Lester E. Johnson

[57] ABSTRACT

Fraction IV, a discard fraction of the Cohn fractionation scheme, may be used as a supplement in cell growth media if the Fraction IV is rendered substantially free of components within the molecular weight range $2.5 \times 10^5 - 1.0 \times 10^{10}$, which components inhibit cell growth.

7 Claims, No Drawings

CELL GROWTH MEDIUM SUPPLEMENT

BACKGROUND OF THE INVENTION

1. Field of the Invention

This invention is related to and has among its objects the provision of novel cell culture media and novel methods of culturing cells. It is a particular object of the invention that the cell culture media be free of non-human proteins. Further objects of the invention will be evident from the following Description wherein parts and percentages are by weight unless otherwise specified.

2. Description of the Prior Art

Human and other mammalian cells are generally grown in a medium containing defined nutrients and a supplement, usually animal blood proteins, particularly fetal calf serum. The use of animal serum proteins requires extensive purification of the product grown in the medium, especially where the cell-induced product is for human use such as in the case of a hybridoma antibody preparation or interferon production. It is, thus, preferred to utilize homologous proteins of human origin as a supplement in these cell cultures if such proteins may be found.

Keay in *Biotechnology and Bioengineering*, 18, 363, (1976) describes the use of an autoclavable, low cost, serum-free medium consisting of minimum essential nutrients, bactopeptones, and insulin. The author demonstrated that the cell growth of five different cell lines was about the same as those propagated in conventional systems containing animal blood proteins.

The invention disclosed in U.S. Pat. No. 4,198,479 (hereinafter '479) provides an improved process for the growth of lymphoblastoid cells, such as, for example, Namalva cells, in a medium supplemented with human albumin. The invention further provides for the production of interferon by viral infection of these lymphoblastoid cells in a medium also supplemented with human albumin.

One problem with the use of human albumin in cell culture media is that albumin, a therapeutically useful product, is consumed. Since the supply of this raw material is limited, it is disadvantageous to direct a portion of this material to a non-therapeutic use. Furthermore, human albumin is expensive and, thus, apparently would increase the cost of the cell culturing activity and the products made thereby.

Lambert et al in *J. Cell Sci.*, 35, 381–392, 1979, disclose a "polypeptide" with a growth factor activity in the less than 10,000 Daltons fraction (NSILA method of purification of calf serum, Rinderknecht et al, *Proc. natn. Acad. Sci. USA*, 73, 2365–2369, 1976). This fraction was used in the absence of whole serum in a growth medium. In attempts by the authors to purify the growth factor it was found that growth factor activity could be recovered, particularly in fraction IV, in fractions of serum prepared by the cold ethanol method of fractionation (Cohn et al, *J. Am. Chem. Soc.*, 68, 459–475, 1956).

Recently, Maciag et al disclosed (*Science*, 1981, Vol. 211, 1452–1454) a cell culture medium consisting of Medium 199 containing epidermal growth factor, triiodothyronine, hydrocortisone, Cohn Fraction IV, insulin, transferrin, bovine brain extract, and trace elements. The Cohn Fraction IV, a potent source of insulin-like growth factors, was prepared by extraction in acetic acid for 2 hours followed by gentle boiling for 30 minutes, conditions known to result in protein denaturation. The extract was centrifuged, neutralized, dialyzed, and lyophilized.

SUMMARY OF THE INVENTION

We have discovered that Fraction IV, a discard fraction of the Cohn fractionation scheme, may be used directly as a supplement in growth medium for cell culturing. It is known that Fraction IV contains albumin as well as tissue growth factors, hormones, and other proteins (Schultz et al, "Molecular Biology of Human Proteins", Vol. 1, page 252, Elsevier, New York, 1966). It is also known that Fraction IV-1, an intermediate fraction in the aforementioned Cohn fractionation, contains substantial amounts of albumin, although less than the amount in Fraction IV, as well as the other above-mentioned components. Thus, in view of the teaching of '479 it would be expected that both Fraction IV-1 and Fraction IV could function as supplements in a cell growth medium.

Surprisingly, we discovered that Fraction IV is a much better supplement in growth medium for cell culturing than Fraction IV-1. Indeed, Fraction IV-1 did not support growth and, in most cases, actually led to destruction of existing cells.

The invention, thus, comprises Fraction IV substantially free from components which inhibit cell growth, said components being in the molecular weight range of about $2.5 \times 10^5 - 1.0 \times 10^{10}$. The invention further comprises novel methods of preparing the Fraction IV of the invention, methods of using the so-prepared material in production of a cell culture medium, and methods of producing a product, whose growth is induced by such means as viral induction, using this cell culture medium supplemented with the Fraction IV of the invention.

The Cohn Fraction IV is rendered suitable as a supplement in a cell culture medium by a process which involves holding an aqueous mixture containing Fraction IV for a period of time and at a temperature sufficient to render substantially all components which inhibit cell growth separable from the mixture and then separating these components.

The primary advantage of the invention is that the problem of the presencee of non-human proteins in the cultured cells is avoided. Thus, the need for extensive purification procedures to remove such proteins is obviated. Proteins produced in the growth medium of the invention may be employed without purification to remove non-human proteins.

An important advantage of the invention involves both conservational and economical aspects. As mentioned above, Fraction IV presently is a discard fraction in the Cohn fractionation method. Albumin, on the other hand, is a useful therapeutic protein in limited supply. Thus, the instant invention makes unnecessary the use of albumin as a supplement in a growth medium thereby not diverting albumin from its role in therapeutics. Furthermore, albumin is expensive, which would add to the cost of the growth medium and the cells and/or proteins produced using such medium. Since Fraction IV is currently a discard or unused fraction in the Cohn fractionation scheme, it is anticipated that the cost of this material, and, consequently, products grown in a medium supplemented with this material, would be much less than in situations where albumin is used as a supplement.

DESCRIPTION OF THE PREFERRED EMBODIMENTS

One aspect of the invention involves Fraction IV substantially free from components which inhibit cell growth, said components being in the molecular weight range of about $2.5 \times 10^5 - 1.0 \times 10^{10}$, and methods of its production. This material is referred to herein as "Fraction IV-CGMS" (Cell Growth Media Supplement). The starting material for the novel substance of the invention is Fraction IV of the Cohn fractionation scheme disclosed in Cohn et al, *J. Am. Chem. Soc.*, Vol. 68, 459 (1946) and in Oncley et al, ibid., Vol. 71, 541 (1949) and subsequent variations thereof which, although modified, still yield a Fraction IV. The term "Cohn Fraction IV" shall therefore be used to designate any Fraction IV so-produced.

In the preparation of Fraction IV-CGMS Cohn Fraction IV is prepared and mixed with water. The amount of water is not critical; generally, water is added to obtain the protein concentration desired in the final product. Typically, about 3–5 parts of water are used per part of Cohn Fraction IV. The resulting mixture is held, or preferably agitated by stirring, shaking, or the like, for a period of about 1–2 hours, at a temperature of about 2°–10° C. and then treated to remove substantially all components which inhibit cell growth, which components have been precipitated. To this end the mixture may be subjected to centrifugation for a period of about 1–2 hours. Alternately, the mixture may be filtered. Other modes of accomplishing the above result will be suggested to those skilled in the art. The above treatment also places the Fraction IV in a condition for sterilization.

The supernatant fluid from the centrifugation step, after separation from the residue, may be subjected to pH adjustment, dialysis, sterilization, pasteurization, lyophilization and the like prior to use as a growth medium supplement. The pH of Fraction IV-CGMS should be compatible with its intended use. Generally, the pH is governed by the requirements of the cells to be grown in a medium supplemented with Fraction IV-CGMS. The mixture can be dialyzed, sterilized, and pasteurized according to known procedures. Prior to sterilization it may be desirable to adjust the protein concentration of the mixture to a level sufficient to provide a growth-medium-supplementing amount of protein in the mixture. Fraction IV-CGMS prepared in the above manner contains protein in its native state and is electrophoretically-free (substantially free) of components within the molecular weight range of about $2.5 \times 10^5 - 1.0 \times 10^{10}$. In other words, the presence of such components cannot be detected by electrophoresis. The Fraction IV-CGMS of the invention may be packaged as a sterile, lyophilized material. Alternatively, the present product can be packaged as an aqueous solution.

To prepare a growth medium in accordance with the invention, one proceeds as in conventional practice. Accordingly, certain nutrients are combined to form a medium to which is added Fraction IV-CGMS as a supplement in place of fetal calf serum or albumin.

The use of Fraction IV-CGMS is next described in detail with reference particularly to the growth of Namalva cells (lymphoid type). This is by way of illustration only and is not meant to limit the invention. In its broad ambit, the Fraction IV-CGMS of the invention can be used as a substitute for fetal calf serum (FCS) in all situations where FCS is employed as a supplement in a growth medium. Thus, the material of the invention can be used as a supplement in growth media to grow cell lines and cell strains of the fibroblastic, epithelial, and lymphoid type.

Nutrient media for cell culture generally contain inorganic metal ion salts, carbohydrates, amino acids, vitamins, and other components. One such synthetic medium is Medium RPMI/1640 (manufactured by Grand Island Biological Company, Grand Island, N.Y.). The medium was developed at Roswell Park Memorial Institute and was designed specifically for growing human and mouse leukemia cells. For purposes of the invention this medium is supplemented with enough Fraction IV-CGMS to yield adequate cell growth. For example, the medium may be supplemented with about 1–15% solution of Fraction IV-CGMS.

The so-prepared medium is then seeded with the viable Namalva cells at a concentration sufficient to induce Namalva cell growth and held at a pH and temperature and for a time sufficient to grow the desired concentration of Namalva cells. The conditions are similar to those in the art where FCS or albumin are used as a supplement.

The culture grown as above can be used for the production of a product by first diluting the culture with fresh synthetic medium containing Fraction IV-CGMS to a Namalva cell concentration sufficient to produce the induced product. The production of product is induced by addition of an appropriate material such as a virus in a concentration sufficient to induce production. The culture is incubated for a time and at a temperature sufficient to produce the product. The so-produced material is isolated from the culture by conventional techniques.

EXAMPLES

The invention is further demonstrated by the following illustrative examples.

EXAMPLE 1

Preparation of Fraction IV-CGMS

The aforementioned Cohn fractionation was employed to obtain the above product. Briefly, gamma globulin was first removed from the cryoprecipitate-poor plasma. Ethanol was then added to a final concentration of 40%. At a pH value of 6.05 and at a temperature of $-5°$ C. or lower, a protein precipitate, designated as Fraction IV, was formed. The precipitate was frozen, cut into small pieces approximately 5 mm$^3$ and combined with water-for-injection in a proportion of 4 ml per gram of material. The resulting mixture was stirred at 5° C., and then subjected to centrifugation at 6,000 rpm. The pH of the Fraction IV water extract (supernatant) was adjusted to 6.9 before dialysis against 2000 volumes of 0.85% NaCl. The dialysate was then sterilized by filtration using a 0.45u Millipore Sterifil(TM) filter unit. Protein composition of a typical extract is shown in Table I. If necessary, the protein content was adjusted to $5 \pm 0.3\%$ (comparable to fetal calf serum) before sterile filtration.

Electrophoresis was carried out in 4% polyacrylamide gel and in the presence of 0.2% sodium dodecyl sulfate (SDS). The gels were stained for one hour with Coomassie Brilliant Blue. After destaining in 7.5% acetic acid, densitometry was performed with a Gilford 250 spectrophotometer equipped with a linear gel transport and an electronic integrating recorder (Gilford Instrument, Oberlin, OH).

Protein content was measured by a Biuret assay.

Albumin content was measured by radial immodiffusion test (M-Partigen(TM), Calbiochem—Behring Corp., La Jolla, CA).

TABLE 1

Protein Analyses in Fraction IV-CGMS
SDS Electrophoresis

| MW estimate | % of Composition | Protein Content | Albumin Content |
|---|---|---|---|
| 63,000 | 55 | 4.90% | 2620 mg/dl |
| 82,000 | 38 | | |
| 136,000 + 153,000 | 9 | | |

EXAMPLE 2

Growth of Namalva Cells

A batch of Namalva cells, obtained from Frederick Cancer Research Center, Frederick, MD, was aliquoted into the requisite number of centrifuge tubes and centrifuged to pellet the cells. The supernatant fluid was discarded, and the cells were resuspended in medium containing the desired concentration (10%, 5%, 2.5%, 1%) of different batches (A-E) of Fraction IV-CGMS prepared as in Example 1 (or fetal calf serum or albumin as a control). The cell suspensions were then added to 75 cm$^2$ tissue culture flasks and incubated at 37° C. Each day a sample of cells was removed from each flask and counted by means of a Coulter counter. The growth of Namalva cells was studied over a 96-hour period of incubation since under normal conditions this period of time is required to reach maximum cell numbers. The growth ratio, defined as cell count on Day 4 divided by cell count on Day 1, and the population doubling time, defined as $$\frac{48 \ln 2 \text{ hr.}}{\ln\left(\frac{\text{cell count on Day 3}}{\text{cell count on Day 1}}\right)}$$

were ascertained. The results are summarized in Tables 2A and 2B, respectively.

TABLE 2A

Growth Ratio of Namalva Cells in Medium Containing Various Concentrations of Fraction IV-CGMS

| Sample | Growth Ratio | | | |
|---|---|---|---|---|
| | 10% | 5% | 2.5% | 1% |
| A Fraction IV-CGMS | 4.1 | 3.7 | 3.6 | 3.2 |
| B Fraction IV-CGMS | 4.2 | 4.4 | 4.7 | 3.9 |
| C Fraction IV-CGMS | 5.1 | 4.7 | 3.8 | 3.5 |
| D Fraction IV-CGMS | 4.5 | 4.5 | 3.7 | 3.6 |
| E Fraction IV-CGMS | 3.9 | 4.5 | 4.6 | 4.4 |
| Control (Fetal Bovine Serum) | 5.1 | 4.8 | 4.2 | 3.3 |
| Control (Albumin) | 2.6 | 3.1 | 3.3 | 3.1 |

TABLE 2B

Population Doubling Time of Namalva Cells in Medium Containing Various Concentrations of Fraction IV-CGMS

| Sample Identification | Population Doubling Time (hr) | | | |
|---|---|---|---|---|
| | 10% | 5% | 2.5% | 1% |
| A Fraction IV-CGMS | 24.9 | 27.0 | 27.6 | 28.4 |
| B Fraction IV-CGMS | 27.7 | 25.8 | 24.0 | 29.7 |
| C Fraction IV-CGMS | 23.2 | 24.8 | 28.0 | 29.4 |
| D Fraction IV-CGMS | 27.0 | 24.7 | 27.4 | 29.8 |
| E Fraction IV-CGMS | 27.0 | 26.0 | 24.8 | 27.3 |
| Control (Fetal Bovine Serum) | 22.0 | 23.0 | 25.9 | 30.7 |

EXAMPLE 3

Fraction IV-1 as a Growth Medium Supplement

This example is not in accordance with the present invention but is provided for purposes of comparison.

Fraction IV-1 was obtained according to the fractionation scheme of Cohn et al, supra, and was treated according to the procedure of Example 1 as applied to Fraction IV. The protein analysis of Fraction IV-1 is as follows:

Protein Analyses in Fraction IV-1
SDS Electrophoresis

| MW estimate | % of Composition | Protein Content | Albumin Content |
|---|---|---|---|
| 39,810 | 4% | 4.75% | 1724 mg/dl |
| 51,280 | 42% | | |
| 66,070 | 24% | | |
| 131,800 | 25% | | |
| 309,700 | 5% | | |

The procedure of Example 2 for growth of Namalva cells was followed using Fraction IV-1 prepared above in place of Fraction IV. The growth ratio of Namalva cells in the medium supplemented with Fraction IV-1 is summarized in Table 3.

TABLE 3

| Sample | Growth Ratio | | |
|---|---|---|---|
| | 10% | 5% | 2.5% |
| Fraction IV-1 | 0.6 | 0.8 | 1.0 |
| Control (Fetal Bovine Serum) | 5.1 | 4.8 | 4.2 |

We claim:

1. In a medium for the growth of mammalian cells containing nutrients and protein supplement, the improvement wherein the protein supplement consists entirely of human proteins and comprises Cohn Fraction IV treated to be substantially free of components within the molecular weight range $2.5 \times 10^5 - 1.0 \times 10^{10}$.

2. The composition of claim 1 further comprising vitamins, minerals, amino acids, carbohydrates, and other nutrients necessary for the growth of cells.

3. In a method for growing cells, comprising forming a cell growth medium containing vitamins, minerals, amino acids, carbohydrates, and other nutrients necessary for growth of cells and a cell growth supplement in an amount sufficient to grow the cells, seeding the cell growth medium with viable cells to be grown, inducing the growth of the cells in said medium, and recovering the cells from the medium, the improvement which comprises using Cohn Fraction IV which has been treated to be substantially free of growth inhibiting components within the molecular weight range of about $2.5 \times 10^5$ to $1.0 \times 10^{10}$ as the cell growth supplement.

4. A method for rendering Fraction IV obtained from human blood according to the Cohn fractionation method suitable as a supplement in cell culture media, which comprises
   (a) holding a aqueous mixture containing Fraction IV for a period of 1–2 hours and at a temperature of 2°–10° C. to render substantially all components which inhibit cell growth separable from the mixture;
   (b) separating the so-rendered components from the mixture.

5. The method of claim 4 wherein the aqueous mixture is agitated during the holding period.

6. The method of claim 4 wherein the so-rendered components are separated from the mixture in Step b by centrifugation.

7. The method of claim 4 wherein the mixture in Step b is centrifuged for a period of time and at a velocity sufficient to separate all the so-rendered components from the mixture.

* * * * *